(12) United States Patent
Kim et al.

(10) Patent No.: US 9,422,601 B2
(45) Date of Patent: Aug. 23, 2016

(54) METHOD OF DETERMINING A RATIO OF RNA SPECIES IN A SAMPLE

(71) Applicant: Samsung Electronics Co., Ltd., Suwon-si, Gyeonggi-do (KR)

(72) Inventors: Sea-hee Kim, Seoul (KR); Joo-won Rhee, Yongin-si (KR); Ko-bong Choi, Osan-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 4 days.

(21) Appl. No.: 13/715,928

(22) Filed: Dec. 14, 2012

(65) Prior Publication Data

US 2013/0157269 A1 Jun. 20, 2013

(30) Foreign Application Priority Data

Dec. 15, 2011 (KR) .......................... 10-2011-0135776
Nov. 16, 2012 (KR) .......................... 10-2012-0130504

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |
| *C07H 21/00* | (2006.01) |

(52) U.S. Cl.
CPC .................................. *C12Q 1/6851* (2013.01)

(58) Field of Classification Search
USPC ........... 435/6.1, 6.11, 6.12, 91.1, 91.2, 91.51; 436/94, 501; 536/23.1, 24.3, 24.33, 536/25.3
See application file for complete search history.

(56) References Cited

U.S. PATENT DOCUMENTS

| | | | |
|---|---|---|---|
| 6,251,639 | B1 | 6/2001 | Kurn |
| 6,977,153 | B2 | 12/2005 | Kumar et al. |
| 7,049,133 | B2 | 5/2006 | Kaempfer et al. |
| 7,846,666 | B2 | 12/2010 | Kurn |
| 2006/0188893 | A1 | 8/2006 | Kumar et al. |
| 2009/0042192 | A1 | 2/2009 | Kiefer et al. |
| 2011/0189679 | A1 | 8/2011 | Kurn et al. |

FOREIGN PATENT DOCUMENTS

JP 2006180884 A 7/2006

OTHER PUBLICATIONS

The definition of "ratio" from Wikipedia, the free encyclopedia. Printed on Mar. 16, 2015.*
Torchia et al., "Achaeal RNA Ligase is a Homodimeric Protein that Catalyzes Intramolecular Ligation of Single-Stranded RNA and DNA," *Nucleic Acids Research*, 36(19): 6218-6227 (2008).
Chu, Yongjun et al. "Intramolecular circularization increases efficiency of RNA sequencing and enables CLIP-Seq of nuclear RNA from human cells", *Nucleic Acids Research*, doi:10.1093; pp. 1-13 (2015).

* cited by examiner

*Primary Examiner* — Frank Lu
(74) *Attorney, Agent, or Firm* — Leydig, Voit & Mayer, Ltd.

(57) ABSTRACT

A method of amplifying DNA from RNA in a sample by using circular RNA is provided.

19 Claims, 6 Drawing Sheets

```
                        SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Synthetic (forward primer)

<400> SEQUENCE: 1
ccactttgcc tttctctcca                                               20

<210> SEQ ID NO 2
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 2
cattcatttg tttacatctg gc                                            22

<210> SEQ ID NO 3
<211> LENGTH: 20
<212> TYPE: DNA
<213> ORGANISM: Artificial Sequence
<220> FEATURE:
<223> OTHER INFORMATION: Synthetic (template specific primer)

<400> SEQUENCE: 3
ggaaacggat gataactggt                                               20

<210> SEQ ID NO 4
<211> LENGTH: 23
<212> TYPE: DNA
<213> ORGANISM: Artificial Sequence
<220> FEATURE:
<223> OTHER INFORMATION: Synthetic (cDNA binding primer)

<400> SEQUENCE: 4
acattcattt gtttacatct ggc                                           23

<210> SEQ ID NO 5
<211> LENGTH: 20
<212> TYPE: DNA
<213> ORGANISM: Artificial Sequence
<220> FEATURE:
<223> OTHER INFORMATION: Synthetic (downstream primer for actin)

<400> SEQUENCE: 5
gtcatagtcc gcctagaagc                                               20

<210> SEQ ID NO 6
<211> LENGTH: 17
<212> TYPE: DNA
<213> ORGANISM: Artificial Sequence
<220> FEATURE:
<223> OTHER INFORMATION: Synthetic (downstream primer for GUSB)

<400> SEQUENCE: 6
gccctgactc ggggagg                                                  17

<210> SEQ ID NO 7
```

```
<211> LENGTH: 21
<212> TYPE: DNA
<213> ORGANISM: Artificial Sequence
<220> FEATURE:
<223> OTHER INFORMATION: Synthetic (downstream primer for TFRC)

<400> SEQUENCE: 7
cagccactgt aaactcaggc c                                          21

<210> SEQ ID NO 8
<211> LENGTH: 40
<212> TYPE: DNA
<213> ORGANISM: Artificial Sequence
<220> FEATURE:
<223> OTHER INFORMATION: Synthetic (upstream primer for actin)

<400> SEQUENCE: 8
gaaattaata cgactcacta tacctggcct cgctgtccac                      40

<210> SEQ ID NO 9
<211> LENGTH: 40
<212> TYPE: DNA
<213> ORGANISM: Artificial Sequence
<220> FEATURE:
<223> OTHER INFORMATION: Synthetic (upstream primer for GUSB)

<400> SEQUENCE: 9
gaaattaata cgactcacta taccaggtat ccccactcag                      40

<210> SEQ ID NO 10
<211> LENGTH: 41
<212> TYPE: DNA
<213> ORGANISM: Artificial Sequence
<220> FEATURE:
<223> OTHER INFORMATION: Synthetic (upstream primer for TFRC)

<400> SEQUENCE: 10
gaaattaata cgactcacta tacctggact atgagaggta c                    41

<210> SEQ ID NO 11
<211> LENGTH: 21
<212> TYPE: DNA
<213> ORGANISM: Artificial Sequence
<220> FEATURE:
<223> OTHER INFORMATION: Synthetic (B-actin_F)

<400> SEQUENCE: 11
cagcagatgt ggatcagcaa g                                          21

<210> SEQ ID NO 12
<211> LENGTH: 18
<212> TYPE: DNA
<213> ORGANISM: Artificial Sequence
<220> FEATURE:
<223> OTHER INFORMATION: Synthetic (B-actin_R)

<400> SEQUENCE: 12
gcatttgcgg tggacgat                                              18

<210> SEQ ID NO 13
<211> LENGTH: 23
<212> TYPE: DNA
<213> ORGANISM: Artificial Sequence
<220> FEATURE:
<223> OTHER INFORMATION: Synthetic (B-actin_P)

<400> SEQUENCE: 13
```

```
aggagtatga cgagtccggc ccc                                              23
```

<210> SEQ ID NO 14
<211> LENGTH: 20
<212> TYPE: DNA
<213> ORGANISM: Artificial Sequence
<220> FEATURE:
<223> OTHER INFORMATION: Synthetic (GAPDH_F)

<400> SEQUENCE: 14

```
attccaccca tggcaaattc                                                  20
```

<210> SEQ ID NO 15
<211> LENGTH: 22
<212> TYPE: DNA
<213> ORGANISM: Artificial Sequence
<220> FEATURE:
<223> OTHER INFORMATION: Synthetic (GAPDH_R)

<400> SEQUENCE: 15

```
gatgggattt ccattgatga ca                                               22
```

<210> SEQ ID NO 16
<211> LENGTH: 22
<212> TYPE: DNA
<213> ORGANISM: Artificial Sequence
<220> FEATURE:
<223> OTHER INFORMATION: Synthetic (GAPDH_P)

<400> SEQUENCE: 16

```
ccgttctcag ccttgacggt gc                                               22
```

<210> SEQ ID NO 17
<211> LENGTH: 20
<212> TYPE: DNA
<213> ORGANISM: Artificial Sequence
<220> FEATURE:
<223> OTHER INFORMATION: Synthetic (GUSB_F)

<400> SEQUENCE: 17

```
cccactcagt agccaagtca                                                  20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic (GUSB_R)

<400> SEQUENCE: 18

```
cacgcaggtg gtatcagtct                                                  20
```

<210> SEQ ID NO 19
<211> LENGTH: 27
<212> TYPE: DNA
<213> ORGANISM: Artificial Sequence
<220> FEATURE:
<223> OTHER INFORMATION: Synthetic (GUSB_P)

<400> SEQUENCE: 19

```
tcaagtaaac gggctgtttt ccaaaca                                          27
```

<210> SEQ ID NO 20
<211> LENGTH: 24
<212> TYPE: DNA

```
<213> ORGANISM: Artificial Sequence
<220> FEATURE:
<223> OTHER INFORMATION: Synthetic (RPLPO_F)

<400> SEQUENCE: 20
ccattctatc atcaacgggt acaa                                          24

<210> SEQ ID NO 21
<211> LENGTH: 23
<212> TYPE: DNA
<213> ORGANISM: Artificial Sequence
<220> FEATURE:
<223> OTHER INFORMATION: Synthetic (RPLPO_R)

<400> SEQUENCE: 21
tcagcaagtg ggaaggtgta atc                                           23

<210> SEQ ID NO 22
<211> LENGTH: 25
<212> TYPE: DNA
<213> ORGANISM: Artificial Sequence
<220> FEATURE:
<223> OTHER INFORMATION: Synthetic (RPLPO_P)

<400> SEQUENCE: 22
tctccacaga caaggccagg actcg                                         25

<210> SEQ ID NO 23
<211> LENGTH: 20
<212> TYPE: DNA
<213> ORGANISM: Artificial Sequence
<220> FEATURE:
<223> OTHER INFORMATION: Synthetic (TFRC_F)

<400> SEQUENCE: 23
gccaactgct ttcatttgtg                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic (TFRC_R)

<400> SEQUENCE: 24
actcaggccc atttccttta                                               20

<210> SEQ ID NO 25
<211> LENGTH: 28
<212> TYPE: DNA
<213> ORGANISM: Artificial Sequence
<220> FEATURE:
<223> OTHER INFORMATION: Synthetic (TFRC_P)

<400> SEQUENCE: 25
agggatctga accaatacag agcagaca                                      28
```

METHOD OF DETERMINING A RATIO OF RNA SPECIES IN A SAMPLE

CROSS-REFERENCE TO RELATED APPLICATION

This application claims the benefit of Korean Patent Application Nos. 10-2011-0135776, filed on Dec. 15, 2011, and 10-2012-0130504, filed on Nov. 16, 2012, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 5,247 Byte ASCII (Text) file named "711881_ST25.txt," created on Dec. 14, 2012.

BACKGROUND

1. Field

The present disclosure relates to methods of determining a ratio of RNA species in a sample by amplifying target RNA in a sample into DNA without a bias.

2. Description of the Related Art

Transcriptome analysis is an important approach to diagnose a disease, detect an underlying cause of a disease, and/or find new targets for drug development. In the transcriptome analysis, a small amount of RNA obtained from a sample needs to be amplified.

RNA expressed from a cell or a virus has a structure with intrinsic activity. For example, mRNA of a eukaryotic cell has a 5'-cap structure and a 3'-poly (adenylate) sequence. However, these groups may be removed or deformed for a least a portion of the RNA while a biological sample is stored or analyzed. For example, RNA isolated from a formalin-fixed paraffin-embedded (FFPE) tissue that is frozen or stored at room temperature has a length of about 300 bp or less, indicating degradation of RNA in the sample. The FFPE method is widely used to preserve samples of patients' tissues at room temperature because it is a simple and inexpensive method. FFPE samples of many patients which are preserved for a long period of time provide an invaluable resource for the retrospective study of disease. However, most RNA isolated from a FFPE tissue are fragmented, making it difficult to analyze by conventional methods.

RNA is generally analyzed by reverse transcribing the RNA to produce cDNA, amplifying the cDNA, and assaying the amplified product. However, in such a method, the fragmented RNA may not be converted into cDNA and is, thus, effectively lost when cDNA is synthesized and amplified. This results in a polarization in the analysis of the RNA content of the sample, with certain RNA "species" being underrepresented by the amplified DNA.

Thus, there is a need to develop a method of producing DNA whereby the level of RNA species in a sample is maintained, i.e., the level of RNA species is not polarized. In addition, there is a need to develop a method of determining a ratio of RNA species in a sample in an efficient way.

SUMMARY

Provided are methods of determining a ratio of RNA species in a sample by directly amplifying DNA from RNA in a sample, whereby the level of target RNA species in a sample is not polarized. In one aspect, there is provided a method of determining a ratio of RNA species in a sample, the method comprising: providing a sample comprising two or more different RNAs; incubating the sample in the presence of an enzyme that converts the 5'-cap structure into 5'-monophosphate to convert RNA having a 5'-cap structure into RNA having 5'-monophosphate; incubating the sample in the presence of an enzyme that phosphorylates 5'-OH to convert RNA having 5'-OH into RNA having 5'-monophosphate; incubating the sample in the presence of an enzyme that dephosphorylates a 3'-end to convert RNA having a 3'-phosphate group into RNA having 3'-OH; incubating the sample in the presence of RNA ligase to produce circular RNA; incubating the sample in the presence of RNA-dependent DNA polymerase to produce DNA from the circular RNA; identifying the produced DNA; and determining a ratio of RNA species in the sample based on the identified DNA.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
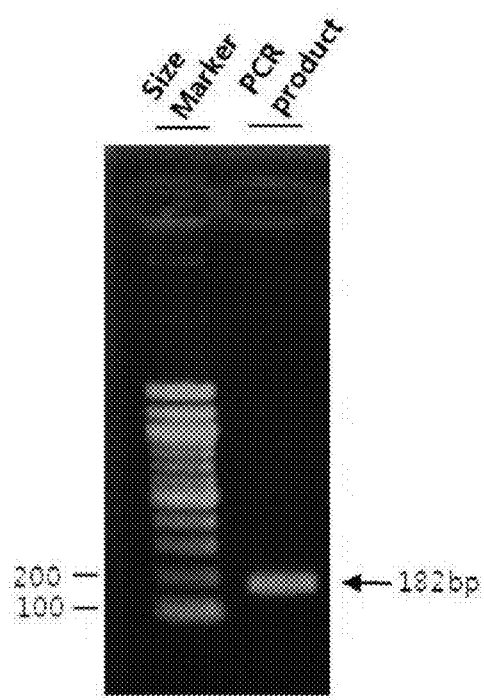
FIG. 1 shows electrophoresis result of PCR products.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a method of determining a ratio of RNA species in a sample, the method including: providing a sample including multiple types of RNA; converting RNA having a 5'-cap structure into RNA having 5'-monophosphate by incubating the sample in the presence of an enzyme that converts the 5'-cap structure into 5'-monophosphate; converting RNA having 5'-OH into RNA having 5'-monophosphate by incubating the sample in the presence of an enzyme that phosphorylates 5'-OH; converting RNA having a 3'-phosphate group into RNA having 3'-OH by incubating the sample in the presence of an enzyme that dephosphorylates a 3'-end; producing circular RNA by incubating the sample in the presence of RNA ligase; producing DNA from the circular RNA by incubating the sample in the presence of RNA-dependent DNA polymerase; identifying the produced DNA; and determining a ratio of RNA species in a sample from the identified DNA.

The method includes providing a sample including multiple types of RNA. The RNA may include natural, synthetic, or semi-synthetic mRNA, tRNA, or rRNA. The sample may be any biological sample or any sample including RNA isolated from the biological sample. The biological sample includes a sample derived from a virus or a living organism. For example, the sample may be selected from the group consisting of blood, saliva, urine, feces, tissues, cells, and biopsy materials. The multiple types of RNA include at least two RNA having different sequences, different lengths, and/or different structures. The sample may include the entire transcriptome of a cell or portions thereof. Isolation of RNA from a biological sample may be performed by using a known method, for example, a Trizol method.

In addition, the sample may be a stored biological sample or any sample including RNA isolated from the biological sample. The sample may be stored by using any method known in the art. For example, the sample may be frozen or formalin-fixed paraffin-embedded (FFPE) tissue of the sample may be stored at room temperature.

The sample may include RNA degradation products isolated from the biological sample. The sample may include RNA isolated from the FFPE tissue. In eukaryotic cells, natural mRNA has a 5'-cap structure and 3'-poly(adenylate) sequence. However, while the biological sample or RNA isolated therefrom is stored or processed, the RNA may degrade. In this case, the degradation products of RNA may not have the 5'-cap structure and 3'-poly(adenylate) sequence. According to an embodiment of the present invention, at least some portion of the RNA of a sample does not have the same structure as the natural RNA. The sample may include at least one (e.g., at least two, at least three, at least four, at least five, or even all) selected from the group consisting of RNA having a 5'-cap structure and 3'-OH; RNA having a 5'-cap structure and 3'-monophosphate; RNA having 5'-OH and 3'-monophosphate; RNA having 5'-OH and 3'-OH; RNA having 5'-monophosphate and 3'-OH; and RNA having 5'-monophosphate and 3'-monophosphate.

The 5'-cap structure may be a structure in which 7-methyl guanylate is linked to a 5'-OH of a sugar of a 5'-end via triphosphate linkage. A 3'-OH and/or 2'-OH of terminal guanylate of the 5' cap structure, and a first and a second nucleotides from the 5'-terminal end may be methylated.

The method includes converting RNA having a 5'-cap structure into RNA having 5'-monophosphate by incubating the sample in the presence of an enzyme that converts a 5'-cap structure into 5'-monophosphate.

The enzyme converting the 5'-cap structure into 5'-monophosphate may include at least one selected from the group consisting of tabacco acid pyrophosphatase (TAP) (e.g., Epicenter Biotechnologies, Catalog No. T81050), Rai1 (Xue, Y. et al. Mol. Cell. Biol. 20, 4006-4015 (2000).), Dom3Z (NCBI Reference Sequence: NP_005501.2), yeast Dcp1 (GenBanK: CAA99170) and Dcp2 (GenBank: ABN58638), and human Dcp1 (NCBI Reference Sequence: NP_060873) and Dcp2 (NCBI Reference Sequence: NP_01229306.1). The incubation may be performed under conditions suitable for converting the 5'-cap structure into 5'-monophosphate. The conditions may be selected by one of ordinary skill in the art according to the selected enzyme. TAP is an enzyme having activity catalyzing hydrolysis of a phosphoric ester bond at a 5'-end of mRNA. The incubation may be performed by using a TAP 10× reaction buffer: 0.5 M sodium acetate (pH 6.0), 10 mM EDTA, 1% β-mercaptoethanol, and 0.1% Triton X-100.

The method includes converting RNA having 5'-OH into RNA having 5'-monophosphate by incubating the sample in the presence of an enzyme that phosphorylates 5'-OH. The enzyme that phosphorylates 5'-OH may be any known enzyme phosphorylating 5'-OH, e.g., kinase. For example, the enzyme phosphorylating 5'-OH may be polynucleotide kinase (PNK) such as T4 polynucleotide kinase (T4 PNK) (e.g., New England BioLabs, Catalog No. M0201L) or variants thereof. The incubation conditions may be selected by one of ordinary skill in the art according to the selected enzyme. The incubation may be conducted under conditions suitable for the phosphorylation of 5'-OH. The PNK such as T4 PNK catalyzes the transfer or exchange of the γ-phosphate from ATP to the 5'-hydroxyl end of polynucleotides (double-stranded and single-stranded DNA and RNA) and nucleoside 3'-monophosphate. The T4 PNK also catalyzes the removal of 3'-phosphoryl groups from 3'-phosphoryl polynucleotides, deoxynucleoside 3'-monophosphate, and deoxynucleoside 3'-diphosphate. Thus, if the T4 PNK is used, the phosphorylation of the 5'-OH and the removal of the 3'-phosphoryl group may be conducted simultaneously or in the same reaction procedure. Further, the incubation for the 5'-decapping in the presence to a 5'-decapping enzyme, the incubation for the 5'-mono-phosphorylation in the presence to a 5'-phosphate kinase, and the incubation for the 3'-dephosphorylation in the presence to a 3'-phosphorylase may be conducted simultaneously, or sequentially, in any order. For example, if an enzyme having at least two activities of a 5'-decapping enzyme, a 5'-phosphate kinase, and a 3'-phosphorylase is used, at least two corresponding incubations may be conducted simultaneously.

The method includes converting RNA having a 3'-phosphate group into RNA having 3'-OH by incubating the sample in the presence of an enzyme that dephosphorylates the 3'-end. The enzyme that dephosphorylates the 3'-end may be any known enzyme dephosphorylating a phosphate group of a 3'-end, e.g., phosphatase. The enzyme dephosphorylating the phosphorelyated 3'-end may be T4 polynucleotide kinase (T4PNK). The incubation may be performed under conditions suitable for dephosphorylating the 3'-end. The conditions may be selected by one of ordinary skill in the art according to the selected enzyme. The phosphorylated 3'-end may be tri-phosphorylated, di-phosphorylated, or mono-phosphorylated.

The sample containing the RNA may be incubated with one or more of the above-referenced types of enzymes (e.g., an enzyme that converts the 5'-cap structure into 5'-monophosphate; an enzyme that phosphorylates 5'-OH; and an enzyme that dephosphorylates a 3'-end) simultaneously or sequentially in any order. If the incubation is performed sequentially, the RNA may, optionally, be isolated between each incubation, or the sequence can be performed without isolating the RNA between incubations. For example, the RNA may be purified after at least one incubations selected from the incubation in the presence of an enzyme that converts the 5'-cap structure into 5'-monophosphate; the incubation in the presence of an enzyme that phosphorylates 5'-OH; and the incubation in the presence of an enzyme that dephosphorylates a 3'-end. The RNA may be purified by a known method, for example, using a commercially available kit, such RNeasy MinElute Cleanup Kit (Qiagen, Catalog. No.

74204). The method may further include incubating the sample in the presence of mono- or di- or tri-phophate removing enzymes such RNA 5' Pyrophosphohydrolase (RppH). The RNA 5' Pyrophosphohydrolase (RppH) removes pyrophosphate from the 5' end of triphosphorylated RNA to leave a 5' monophosphate RNA.

The method includes producing circular RNA by incubating the sample in the presence of RNA ligase. The RNA ligase may be any known enzyme in the art. In addition, the RNA ligase may catalyze intramolecular ligation as known as self-ligation. The RNA ligase, for example, may be T4 RNA ligase 1 (e.g., New England BioLabs, Catalog No. M0204L), T4 RNA ligase 2 (e.g., Ho C K, Shuman S: Proc Natl Acad Sci USA 2002, 99:12709-12714; New England BioLabs, Catalog No. M0239L), CircLigase I (e.g., Epicenter Biotechnologies, 5602 Research Park Blvd., Suite 200 Madison, Wis. 53719, Catalog No. CL4111K), CircLigase II (e.g., Epicenter Biotechnologies, Catalog No. CL9021K), Mth RNA ligase (e.g., Christopher Torchia et al. Nucleic Acids Res. 2008 November; 36(19): 6218-6227; also New England BioLabs, 240 County Road Ipswich, Mass. 01938-2723, Catalog No. E2610L), or any combination thereof. The incubation may be performed under condition suitable for ligating a 5'-monophosphate end and a 3'-OH end. The conditions may be selected by one of ordinary skill in the art according to the selected enzyme. The ligation may be self ligation. The T4 RNA ligase may catalyze the formation of a phosphodiester bond between a 5'-phosphoryl-terminated nucleic acid doner and a 3'-hydroxyl-terminated nucleic acid acceptor in a template-independent manner. The T4 RNA ligase is ATP-dependent and active on a broad range of substrates including RNA, DNA, oligonucleotides, oligodeoxyribonucleotides, and numerous nucleotide derivatives. The incubation may be performed by using a T4 RNA ligase 10× reaction buffer: 330 mM Tris-acetate (pH 7.5), 660 mM potassium acetate, 100 mM magnesium acetate, and 5 mM DTT.

The method includes producing DNA from circular RNA by incubating the sample in the presence of RNA-dependent DNA polymerase. The RNA-dependent DNA polymerase may have reverse transcriptase activity only or DNA polymerase activity together with reverse transcriptase activity. The RNA-dependent DNA polymerase may have strand-displacing DNA polymerase activity. That is, the RNA-dependent DNA polymerase may not only have reverse transcriptase activity but also DNA-dependent DNA polymerase activity. The RNA-dependent DNA polymerase may include Bst DNA polymerase, exonuclease minus (e.g., Lucigen Corp., Middleton, Wis., Simplifying Genomics, Catalog No. 30027-0), Tth polymerase (e.g., Promega Corp, Madison, Wis., Catalog No. M2101), Pyrophage™ 3173 DNA polymerase (e.g., Lucigen Corp., Middleton, Wis., Simplifying Genomics, Catalog No. 30051-1), BcaBEST DNA polymerase (e.g., Takara Bio Inc., Japan, Catalog No. 6046), or any combination thereof. For example, the RNA-dependent DNA polymerase may be Bst DNA polymerase or exconuclease minus. The Bst DNA polymerase and exonuclease minus are a 67 kDa *Bacillus stearothermophilus* DNA polymerase protein (big fragment) that has 5'-3' polymerase activity and strand-displacing activity but does not have 3'-5' exonuclease activity. They also have reverse transcriptase activity. The Bst DNA polymerase and exonuclease minus may be used in isothermal amplification, nucleic acid amplification, whole genome amplification, multiple displacement amplification (MDA), or the like. The incubation may be performed under conditions suitable for reverse transcription and/or DNA-dependent DNA polymerization. The conditions may be selected by one of ordinary skill in the art according to the selected enzyme. The method of producing DNA includes a method of amplifying DNA. The amplification may be performed by using rolling-circle amplification. The rolling-circle amplification is a process of unidirectional nucleic acid replication that may rapidly synthesize multiple copies of circular molecules of DNA or RNA, such as plasmid, the genomes of bacteriophages, and the circular RNA genomes of viroids. Some eukaryotic viruses also amplify their DNA via a rolling circle mechanism. The rolling-circle amplification refers to elongation of a sequence obtained by annealing a random or specific primer to a single-stranded circular nucleic acid and annealing nucleotides to a 3'-OH end of the primer in a template-dependent manner. At a double-stranded region including a portion where the primer is annealed, the sequence may be elongated by displacing the single-stranded DNA from the template by stranded-displacing activity of the DNA polymerase. The primer may include a 3'-OH produced by cleavage of the double-stranded nucleic acid, for example, nicking. The amplification may be performed in the presence of a random primer or a sequence-specific primer. The random primer may have a length in the range of about 5 nt to about 15 nt, for example, may have about a 6 nt-long random sequence. Producing DNA from the circular RNA, in addition to the RNA-dependent DNA polymerase, may include incubating the sample in the presence of separate DNA-dependent DNA polymerase.

According to an embodiment of the present invention, the method may further include adding a poly(adenylate) sequence to the 3'-end by incubating the sample in the presence of poly(adenylate) polymerase before producing the circular RNA. The circular RNA formed by adding the poly (adenylate) sequence to the 3'-end may have a poly(adenylate) sequence regardless of the sequence of the circular RNA. Thus, all RNA contained in the sample may be amplified using a sequence complementary to the poly(adenylate) sequence, for example, oligo dT sequence, as a primer during the amplification process. The amplification is performed in proportion to the amount of circular RNA contained in an original sample. Thus, amplification products may be obtained in proportion to the types of RNA contained in the original sample. Accordingly, the amplification may be performed in the presence of the oligo dT primer. The length of the oligo dT primer may be in the range of 10 to 100 nt, for example, 1 to 50 nt. The poly(adenylate) polymerase may be a poly(A) polymerase I of *Escherichia coli*.

According to the method of producing DNA from RNA in a sample according to an embodiment of the present invention, DNA may be produced from target RNA such that the multiple types of RNA are similar to those of RNA contained in an original sample. That is, specific target RNA is not converted into DNA first, but all target RNA may be uniformly converted into DNA. This is because all target RNA may be converted into circular RNA, but the mechanism is not limited thereto. In the method, the operations may be sequentially performed or all or some operations may be simultaneously conducted.

The method may further include introducing the circular RNA and elements required to the nucleic acid polymerization to inside of droplets after the producing circular RNA. The elements required to the nucleic acid polymerization may include reverse transcriptase, DNA-dependent DNA polymerase, cofactor, buffer, or any combination thereof. The producing DNA from the circular RNA may be performed under isothermal conditions. The producing DNA from the circular RNA may be performed without thermal cycling between about 40° C. and 50° C.

The method may further include introducing an aqueous component that includes at least one of the groups consisting of at least one of the circular RNAs, a primer hybridizable with a part of the circular RNA regions or a complementary sequence to the circular RNA, RNA-dependent DNA polymerase, and DNA-dependent DNA polymerase to inside of micro-compartment of water-in-oil emulsion. Herein, the micro-compartment may be a droplet.

The method of introducing the aqueous component to inside of the micro-compartment of water-in-oil emulsion is known in the art. For example, the aqueous component may be included inside of micro-compartment of water-in-oil emulsion formed by mixing an aqueous component and an oily component. The micro-compartment and the droplet may be used interchangeably. The micro-compartment may have an average diameter that is less than about 10 µm. For example, the micro-compartment may have a diameter in the range of about 100 nm to about 10 µm, about 100 nm to about 5 µm, about 100 nm to about 3 µm, or about 100 nm to about 2 µm.

The oily component refers to a lipophilic component that does not mix with water. The oily component may be mineral oil such silicon oil.

The micro-compartment of water-in-oil emulsion may include a surfactant in addition to the oily component. The surfactant may stabilize the micro-compartment of water-in-oil emulsion or the emulsion status. For example, the surfactant may increase the thermal stability of the emulsion. The surfactant may be also referred to as an emulsifier. The surfactant or emulsifier may include at least one of the group consisting of yolk, lecithin, sodium stearoyl lactylate, emulsifying wax, polysorbate 20, and cetereth 20. The surfactant may be nonionic. The nonionic surfactant may be a nonionic surfactant having hypophilic lipophilic balance (HLB) less than 4. The HLB value may be calculated by Griffin's formula below.

$$HLB = 20 \times MH/M \text{ (MH:molecular mass of hydrophilic portion of a molecule, M:molecular mass of the whole molecule)}$$

The nonionic surfactant may be at least one selected from the group consisting of Span 80 (sorbitan monooleate: Fluka, Japan), Tween 80 (polyoxyethylene sorbitan monooleate: Nakarai, Japan), Triton X-100 (t-octylphenoxypolyethoxyethanol), Sun Soft No. 818 SK (polyglycerol esters of inter-esterified ricinoleic acid: Solar Chemistry, Japan), and Sun Soft O-30 V (glyceryl monooleate: Solar Chemistry, Japan).

The circular RNA may be diluted enough to have less than three molecules in each of the micro-compartments, for example, less than two molecules or less than one molecule.

The primer may be a sequence-specific primer or a random primer. The primer may have a length in the range of about 10 nt to about 100 nt, for example, about 10 nt to about 50 nt, about 10 nt to about 40 nt, about 10 nt to about 30 nt, or about 15 nt to about 30 nt. The random primer may have a length in the range of about 5 nt to about 10 nt. For example, the length of the random primer may be about 5 nt, 6 nt, 7 nt, 8 nt, 9 nt, or 10 nt. In addition, the primer may be a single-stranded DNA. The primer may include reverse primer R only that is complementary to the RNA, or at least one of the group consisting of reverse primer R that is complementary to the RNA or forward primer F that is complementary to the sequences complementary to the RNA.

The RNA-dependent DNA polymerase may include an enzyme having activity of the RNA-dependent DNA polymerase. The RNA-dependent DNA polymerase and reverse transcriptase may be used interchangeably. The RNA-dependent DNA polymerase may be selected from the group consisting of HIV-1 reverse transcriptase derived from human immunodeficiency virus type 1, M-MLV derived from Moloney murine leukemia virus, AMV reverse transcriptase derived from avian myeloblastosis virus, HIV reverse transcriptase, or any combination thereof.

The DNA-dependent DNA polymerase may include an enzyme having activity of the DNA-dependent DNA polymerase. The DNA-dependent DNA polymerase may be selected from the group consisting of Bst DNA polymerase, exonuclease minus, PyroPhage 3173 polymerase, Tth polymerase, and any combination thereof. For example, the Bst DNA polymerase, exonuclease minus are a 67 kDa *Bacillus stearothermophilus* DNA polymerase protein (big fragment) that has 5'-3' polymerase activity and strand-displacing activity but does not have 3'-5' exonuclease activity. The Bst DNA polymerase, exonuclease minus may be used in nucleic acid amplification, and whole genome amplification, MDA, or the like, including isothermal amplification. M-MLV, AMV, HIV reverse transcriptase have activities of reverse transcriptase, ribonuclease, and DNA-dependent DNA polymerase, The Bst DNA polymerase, exonuclease minus are known to have stronger activity of DNA-dependent DNA polymerase compared to the activity of RNA-dependent DNA polymerase. In the presence of the first RNA only, the reverse transcription activity may catalyze the synthesis of DNA from the primer, which is hybridized with the RNA, and once single-stranded DNA is formed, the activity of DNA-dependent DNA polymerase may then work. Therefore, the primer may include a primer complementary to RNA template or a primer complementary to single-stranded DNA produced therefrom.

The aqueous component may further include a reagent for the reverse transcription or the DNA polymerization. The reagent may include a reagent for the RNA-dependent DNA polymerization and/or the DNA-dependent DNA polymerization. The reagents may include buffer, ribonucleotide triphosphate or deoxyribonucleotide triphosphate, and coenzyme or cofactor required for the polymerization.

The RNA may have less than three molecules in each of the micro-compartments in average, for example, less than two molecules or less than one molecule.

According to another embodiment of the present invention, introducing the circular RNA and elements required to nucleic acid polymerization to inside of droplets after producing circular RNA may include preparing at least one circular RNA, the primer complementary to a part of the circular RNA regions or the primer complementary to a complementary sequence to the circular RNA, and aqueous component including the RNA-dependent DNA polymerase and the DNA-dependent DNA polymerase; and manufacturing water-in-oil emulsion by mixing the aqueous component, the oily component, and nonionic surfactant.

During the preparation, the circular RNA, the primer, and the RNA-dependent DNA polymerase and the DNA-dependent DNA polymerase are mixed with the aqueous component such as water or PBS or with buffer. The buffer may be buffer used for DNA polymerization or PCR. The RNA-dependent DNA polymerase and the DNA-dependent DNA polymerase may have at least one molecule in average per each of the micro-compartments.

During the manufacture, the aqueous component, the oily component, and nonionic surfactant may be mixed together. The mixture may or may not be stirred up. In addition, the mixture may be made by applied ultrasonic waves. Description of the aqueous component and the oily component are described above. The nonionic surfactant may have HLB less than 4. The HLB value may be calculated by Griffin's formula represented above. The nonionic surfactant may be at least one selected from the group consisting of Span 80 (sorbitan monooleate: Fluka, Japan), Tween 80 (polyoxyethylene sorbitan monooleate: Nakarai, Japan), Triton X-100 (t-octylphenoxypolyethoxyethanol), Sun Soft No. 818 SK (polyglycerol esters of interesterified ricinoleic acid: Solar Chemistry, Japan), and Sun Soft O-30 V (glyceryl monooleate: Solar Chemistry, Japan).

The method includes identifying (e.g., measuring, quantifying, detecting, and/or analyzing) the produced DNA by identifying the DNA sequence and/or amount of the DNA. The identification of the amount of the DNA may be performed by using a known method, for example, a spectroscopic method, an electrical method, a method to detect DNA by using a detectable marker, or any combination thereof. The identification of the DNA sequence may be performed by using a known method, for example, a chemical method, an electrical method, a hybridization method, or any combination thereof. The chemical method may be a Maxam-Gilbert method, a chain-termination method, or any combination thereof.

The method further includes determining a ratio of RNA species in a sample from the identified DNA. The determination may estimate RNA species each corresponding to the identified DNA species based on the amount thereof.

According to the method, the RNA species in a sample may be converted into DNA without a bias, thus, a ratio of the RNA species in a sample may be determined in an efficient way.

Hereinafter, one or more embodiments will be described in detail with reference to the following examples. However, these examples are not intended to limit the purpose and scope of the invention.

EXAMPLE 1

Circularization and Amplification of RNA Produced by In Vitro Transcription (1) Preparation of RNA DNA having a T7 promoter sequence was amplified by using PCR with pRL-CMV vector plasmid DNA as a template, a forward primer having a nucleotide sequence of SEQ ID NO: 1, and a reverse primer having a nucleotide sequence of SEQ ID NO: 2. mRNA was synthesized from the PCR products including T7 promoter sequences by using Megascript™ Kit (Ambion). In particular, in 1× reaction buffer, about 100 ng of the amplified products, 2 μL of ATP, CTP, UTP, GTP solutions, respectively, and 2 μL of enzyme mixture were all mixed to have a final volume of 20 μL, and the mixture was incubated at 37° C. for about 2 hours. As a result, 100 nt of RNA was obtained in vitro.

Figure 2:
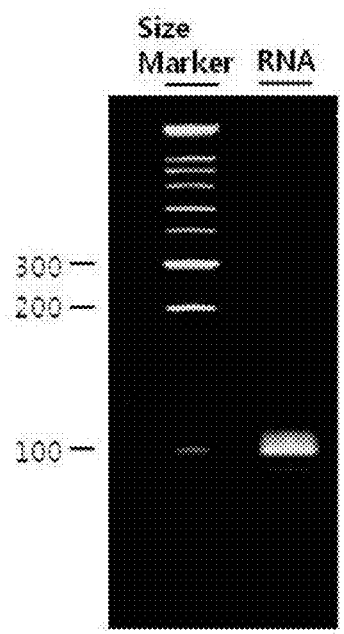
FIG. 2 shows electrophoresis result of in vitro products.

FIG. 1 shows electrophoresis result of PCR products. FIG. 2 shows electrophoresis result of in vitro products.

(2) End-Trimming

The mRNA synthesized in the in vitro transcription of operation (1) has triphosphate at its 5'-end. 300 ng of the synthesized RNA was incubated in the presence of 5 units of RNA 5' pyrophosphatase (RppH) in RppH reaction buffer (50 mM NaCl, 10 mM Tris-Cl, 10 mM MgCl$_2$, 1 mM dithiothreitol (DTT), pH 7.9) at 37° C. for about 30 minutes to obtain RNA having 5'-monophosphate. The RNA 5' Pyrophosphohydrolase (RppH) removes pyrophosphate from the 5' end of triphosphorylated RNA to leave a 5' monophosphate RNA.

(3) Self Ligation 300 ng of RNA having the 5'-monophosphate obtained by RppH treatment was incubated in CircLigase II buffer (33 mM Tris-acetate, pH 7.5, 66 mM potassium acetate, 0.5 mM DTT) after adding MnCl$_2$ and Betaine to have concentrations of 2.5 mM and 1 M, respectively and 100 units of CircLigase II™ at 60° C. for 1 hour. As a result, the 5'-monophosphate end and the 3'-OH end of the mRNA were ligated to obtain circular RNA. The sample was loaded into 10% TBE urea gel (Invitrogen), and the circular RNA that was shifted after self ligation was confirmed by electrophoresis.

Figure 3:
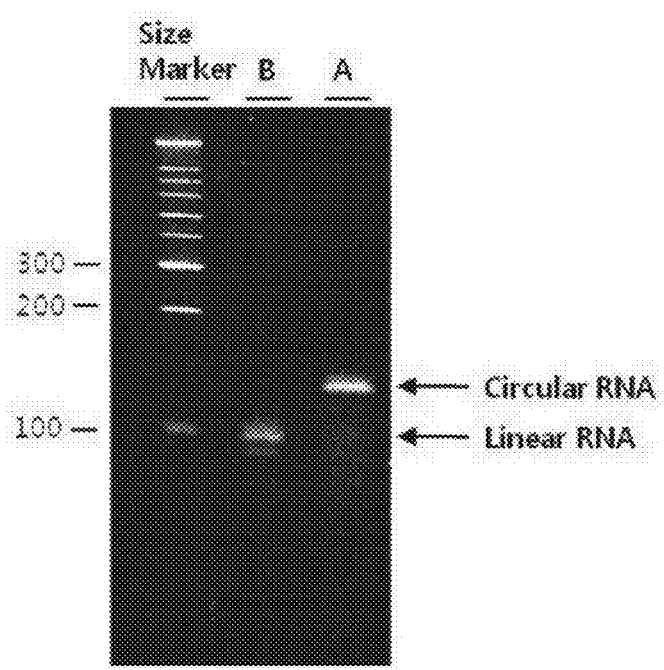
FIG. 3 shows electrophoresis result of products of self ligation.

FIG. 3 shows electrophoresis result of products of self ligation. In FIG. 3, A represent a sample before the ligation, and B represents a sample after the ligation.

(4) Amplification of DNA from RNA

DNA was synthesized from the circular RNA by using enzymes having reverse transcription activity and strand displacing polymerization activity, a primer (SEQ ID NO: 3) that is specific to the circular RNA and a primer (SEQ ID NO: 4) that is able to bind to the synthesized DNA.

Figure 4:
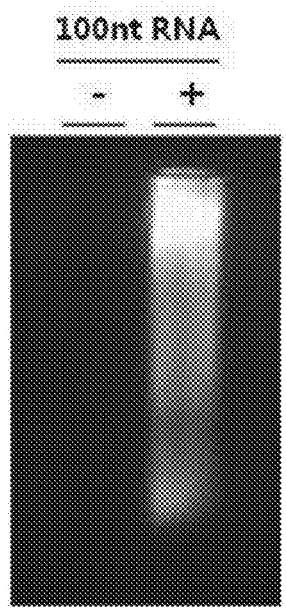
FIG. 4 shows electrophoresis result of products of multiple displacement amplification (MDA) from circular RNA.

In particular, 1.25 μM of the primers (SEQ ID NO: 3 and 4) that are specific to RNA template and 0.16 unit/μl of the Bst DNA polymerase were added to the Bst DNA polymerase buffer (Tris-HCl pH 8.0 52.5 mM, KCl 70 mM, (NH$_2$)$_4$SO$_4$ 8.4 mM, MgCl$_2$ 14 mM, dNTP 1.4 mM, Tween 20 0.12%) and the reaction mixture was incubated at 45° C. for about 2 hours, and accordingly, DNA from the RNA was amplified. As a result, DNA was amplified by a multiple displacement amplification (MDA). FIG. 4 electrophoresis result of products of MDA. In FIG. 4, − and + each represents a control group that does not include 100 nt of the circular RNA and a sample that includes 100 nt of the circular RNA. As shown in FIG. 4, products of DNA amplification were present in the experimental group (+).

EXAMPLE 2

Circularization and Measurement of Amplification Ratio of Three Kinds of RNA Obtained In Vitro Transcription (1) Synthesis of cDNA for Synthesis of 3 Species of Reference RNAs 1× reverse transcriptase buffer (10 mM, Tris-Cl, pH 8.3 at 25° C., 90 mM KCl), 1 mM MnCl$_2$, 0.2 mM dNTP mixture, 15 pmol of each of downstream primer (Actin: SEQ ID. NO: 5, GUSB: SEQ ID. NO: 6, and TFRC: SEQ ID. NO: 7) 1 μL, and 5 units of Tth DNA polymerase (Promega), 1 μg of universal human reference RNA (UHRR) (Stratagene: Cat Nr: 740000) was mixed to have final volume of 20 μL and synthesized the first strand cDNA by incubating at 70° C. for about 20 minutes.

1 μL of each of 15 pmol of upstream primer with T7 promoter sequence (Actin: SEQ ID. NO: 8, GUSB: SEQ ID. NO: 9, and TFRC: SEQ ID. NO: 10), 1× chelate buffer (10 mM Tris-Cl pH 8.3, 100 mM KCl, 0.75 mM EGTA, 0.05% Tween 20, 5% Glycerol), and 0.25 mM MgCl$_2$ was added to 20 μl of the synthesized first strand cDNA sample. Then the sample was incubated at 95° C. for about 5 minutes, followed by another incubation at 70° C. for about 20 minutes to synthesize the second strand cDNA.

Next, by using the cDNA as a template and the upstream primer and the downstream primer, PCR amplification was performed.

Figure 5:
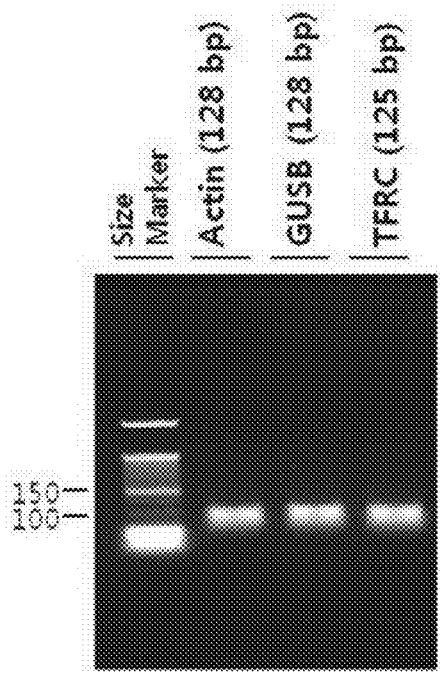
FIG. 5 shows electrophoresis result of PCR products.
Figure 6:
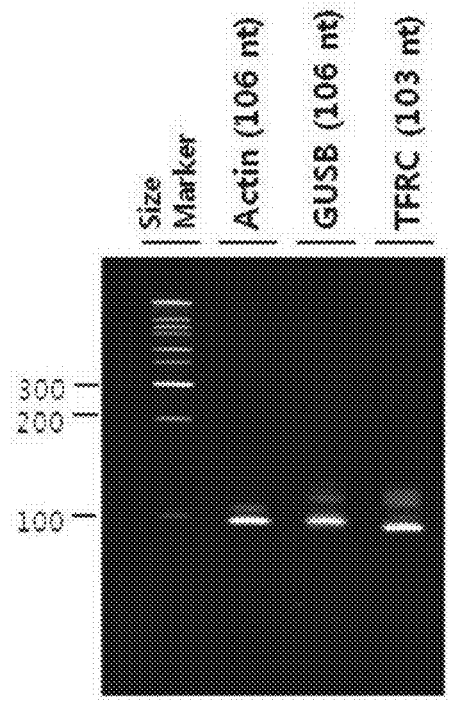
FIG. 6 shows electrophoresis result of in vitro products.

Then, mRNA was synthesized by using Megascript™ T7 Kit (Ambion) that induced transcription by using T7 RNA polymerase from 100 ng of the PRC product. In particular, 100 ng of the PCR product, mixture of 2 μL of ATP, CTP, UTP, and GTP solution, and 2 μL of enzyme mixture were mixed to have total volume of 20 μL and incubated at 37° C. for about 2 hours. FIG. 5 shows electrophoresis result of PCR products, and FIG. 6 shows electrophoresis result of in vitro transcription products. As shown in FIG. 6, 3 kinds of about 100 nt RNA were obtained by in vitro transcription.

(2) End-Trimming

The mRNA that was synthesized during in the in vitro transcription of operation (1) had triphosphate at 5-end. 300 ng of the mRNA was incubated in the presence of 5 units of RNA 5' RppH at 37° C. for about 30 minutes in RppH reaction buffer (50 mM NaCl, 10 mM Tris-Cl, 10 mM MgCl$_2$, 1 mM DTT, pH 7.9), thus RNA having 5'-monophosphate was obtained.

(3) Self Ligation and Isolation of Circular RNA 300 ng of RNA having the 5'-monophosphate obtained by the RppH treatment was incubated in CircLigase™ II buffer (33 mM Tris-acetate, pH 7.5, 66 mM potassium acetate, 0.5 mM DTT) after adding MnCl$_2$ and betaine to have concentrations of 2.5 mM and 1 M, respectively and 100 units of CircLigase II™ at 60° C. for 1 hour. As a result, the 5'-monophosphate end and the 3'-OH end of the mRNA were ligated to obtain circular RNA.

In order to measure accurate amplification fold, the circular RNA was isolated. After loading and performing an electrophoresis of the self-ligation reaction samples in to 10% TBE urea gel (Invitrogen), the self-ligated RNA band was cut from the gel.

By using Midi GeBAflex-tube Gel Extraction & Dialysis Kit (Komabiotech), the circular RNA was extracted from the gel. As a result, 3 kinds of the circular RNA were isolated.

Figure 7:
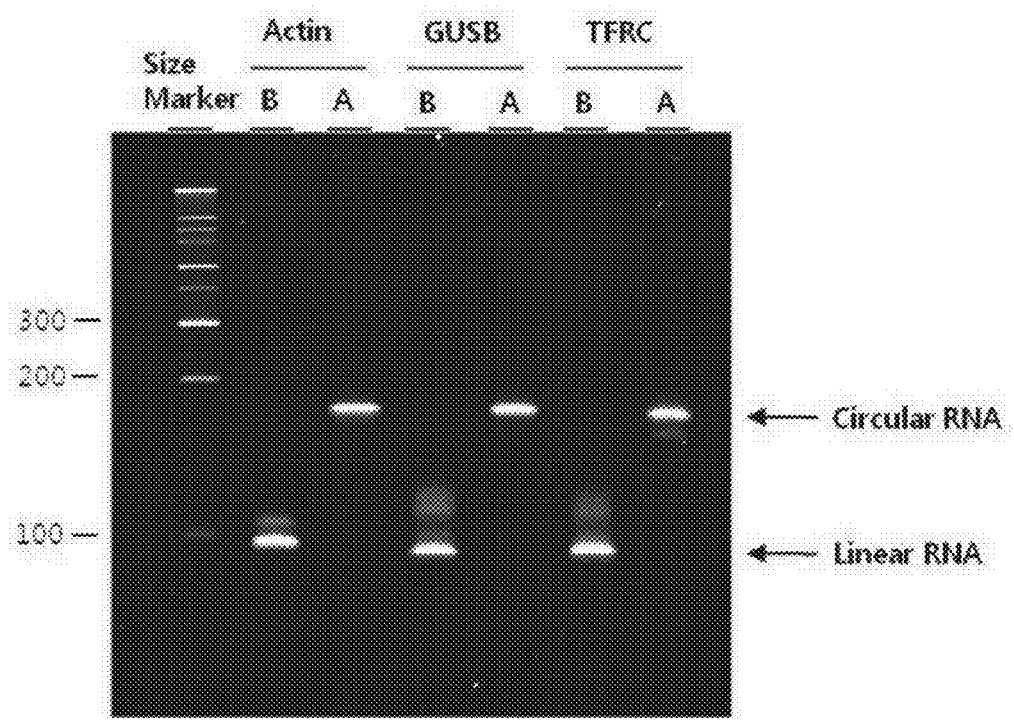
FIG. 7 shows electrophoresis result of products of self ligation.

FIG. 7 shows electrophoresis result of products of self ligation. In FIG. 7, A represents the sample after ligation while B represents the sample before the ligation.

(4) Multiple Displacement Amplification (MDA) Using Emulsion (4.1) Production and Polymerization of Water-in-Oil Droplets In 50 ml of mineral oils, 4.5% (v/v) of Span 80, 0.4% (v/v) of tween 80, and 0.05% (v/v) of Triton X-100 were mixed to obtain oil-surfactant mixture. 400 μl of the oil-surfactant mixture was placed in cryotube vial and mixed while stirring using 3×8 mm stir bar for about 5 minutes at 1000 rpm.

In order to produce emulsion to each of the 3 types of circular RNAs (RNA of Actin, GUSB, and TFRC gene), 3 different aqueous phase were made. 200 μl of the aqueous phase including 2 ng of the circular RNA (40 mM Tris-HCl pH 8.8, 6.4 mM (NH$_4$)$_2$SO$_4$, 53 mM KCl, 10.6 mM MgSO$_4$, 0.1% Triton X-100, 30 μM random hexamer, 1.33 mM dNTPs, 4.8 unit/μl Bst DNA polymerase, 16 unit/μl M-MLV reverse-transcriptase, 40 ng/μl T4 SSB, and 0.2% Antifoam) were added dropwise to the crytobe vial containing the oil-surfactant mixture and mixed while stirring for about 5 minutes at 1000 rpm.

As a result, 3 different emulsions including the aqueous phase were obtained. Droplets obtained from the emulsions had a diameter of 3.33 μm (CV 40%) in average. The droplets included components along with circular RNA, reverse transcription polymerase, and DNA polymerase required for polymerization, and amplification may be performed within the droplets. The circular RNA was diluted enough to include about 50% or less of the total droplets.

(4.2) Polymerization

The emulsion was incubated at 45° C. for about 3, 6, 9, 12, and 15 hours to cause to induce a reverse transcription reaction and DNA-dependent DNA polymerization reaction. After the incubation, RNase was added to the reaction mixture and incubated again to degrade the residual RNA.

After termination of the reaction, the emulsion was centrifuged at 13,000 g for about 5 minutes to remove oil phase. 1 ml of diethyl ether was added to the aqueous phase to destroy droplets of the emulsion and remove mineral oils. The amplified DNA was confirmed by electrophoresis and the amplified DNA was confirmed by using Qubit™ dsDNA HS Assay Kit (Invitrogen).

Figure 8:
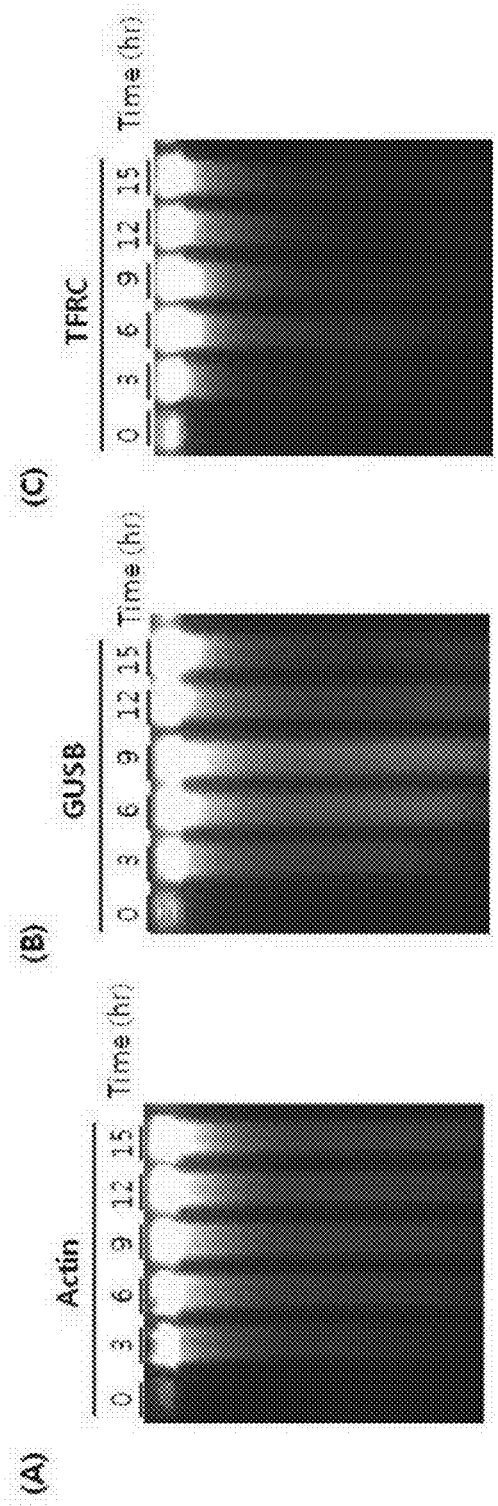
FIG. 8 shows electrophoresis result of products of emulsion amplification, in which (A) is Actin, (B) is GUSB, and (C) is TFRC.

FIG. 8 shows electrophoresis result of products of emulsion amplification. As shown in FIG. 8, it was able to determine the presence of amplified DNA at each reaction time of 3, 6, 9, 12, and 15 hours.

The quantitative results confirmed by using Qubit™ dsDNA HS Assay Kit (Invitrogen) are shown in Table 1.

TABLE 1

| Amplification time (hour) | Actin (μg) | GUSB(μg) | TFRC(μg) |
|---|---|---|---|
| 3 | 40.3 | 26.0 | 18.5 |
| 6 | 60.9 | 48.4 | 40.6 |
| 9 | 62.7 | 54.4 | 44.3 |
| 12 | 62.6 | 54.8 | 49.4 |
| 15 | 63.2 | 52.7 | 54.2 |

As a result in Table 1, 2 ng of RNA at the beginning was approximately 10$^4$-fold amplified. As a result, the circularized RNA may be amplified by the reaction of MDA with high amplification efficiency.

Amplification of the Whole Transcriptome Using Fragmented UHRR.

(1) RNA Preparation: Simulation of Fragmented FFPE RNA

4 μg of UHRR (stratagene) was added to 50 μl of H$_2$O to fragmentize RNA by using Covaris Sonicator for about 5 minutes by irradiating ultrasonic waves.

(2) End Trimming

2 μg of the fragmented RNA was added to 25 units of tobacco acid pyrophosphatase (TAP) in TAP reaction buffer (50 mM sodium acetate pH 6.0, 1 mM EDTA, 0.1% β-mercaptoethanol, 0.01% Triton X-100) to have final volume of 50 μL and obtain decapped RNA by incubating at 37° C. for 1 hour. In the sample, 20 units of T4 PNK was added to 10 μL of 10 mM ATP 1 μL, 10×PNK reaction buffer (700 mM Tris-Cl, 100 mM MgCl$_2$, and 50 mM DTT, pH 7.6) to have final volume of 100 μL and incubated at 37° C. for 30 minutes. As a result, a phosphate group was added to the 5'-OH and 3'-phosphate was removed to have RNA having the 5'-monophosphate and 3'-OH. The T4 PNK has both 5'-kinase activity and 3'-phosphase activity.

(3) Self Ligation 300 ng of RNA having the 5'-monophosphate and 3'-OH obtained by the trimming was incubated in a mixture containing CircLigase™ II buffer (33 mM Tris-acetate, pH 7.5, 0.66 M potassium acetate, 0.5 mM DTT) 2 ul, 1 ul 50 mM MnCl$_2$, 1 ul 5 M betaine and water to 20 ul, and 100 units of CircLigase II™ at 60° C. for 1 hour. As a result, the 5'-monophosphate end and the 3'-OH end of the mRNA were ligated to obtain circular RNA.

In the experiment above, 300 ng of the trimming products was added to 2 μL of 10×XRN-1 reaction buffer (1 M NaCl, 500 mM Tris-Cl, 100 mM MgCl$_2$, 10 mM DTT) with 2 units of XRN1 enzyme (NEB) that had 5'->3' exoribonuclease activity by recognizing the 5'-monophosphate to have final volume of 20 μL and incubated at 37° C. for 1 hour. As a result of electrophoresis of the incubation products, no band was detected, referring to that all the RNAs were degraded. That is, all the 5'-ends of the fragmented UHRR were converted to the 5'-monophosphates. In addition, 300 ng of the trimming products was added to 2 μL of 10× RNaseR reaction buffer (0.2M Tris-Cl pH 8.0, 1 M KCl, 0.1 mM MgCl$_2$) with 2 units of RNaseR enzyme (Epicentre) that had 3'->5' exoribonuclease activity by recognizing the 3'-OH to have final volume of 20 μL and incubated at 37° C. for 1 hour. As a result of electrophoresis of the incubation products, no band was detected, referring to that all the RNAs were degraded. That is, all the 3' ends of the fragmented UHRR were converted to the OH groups.

Also, in the presence of RNaseR enzyme that had 3'->5' exoribonuclease activity by recognizing 3'-OH of the linear RNA, but that is not able to degrade linear RNA wherein 3'-OH is not exposed, 300 ng of self ligation products was incubated at 37° C. for 1 hour. As a result of electrophoresis of the incubation products, bands were detected, referring to that the fragmented UHRR was self-ligated by RNA ligase.

Figure 9:
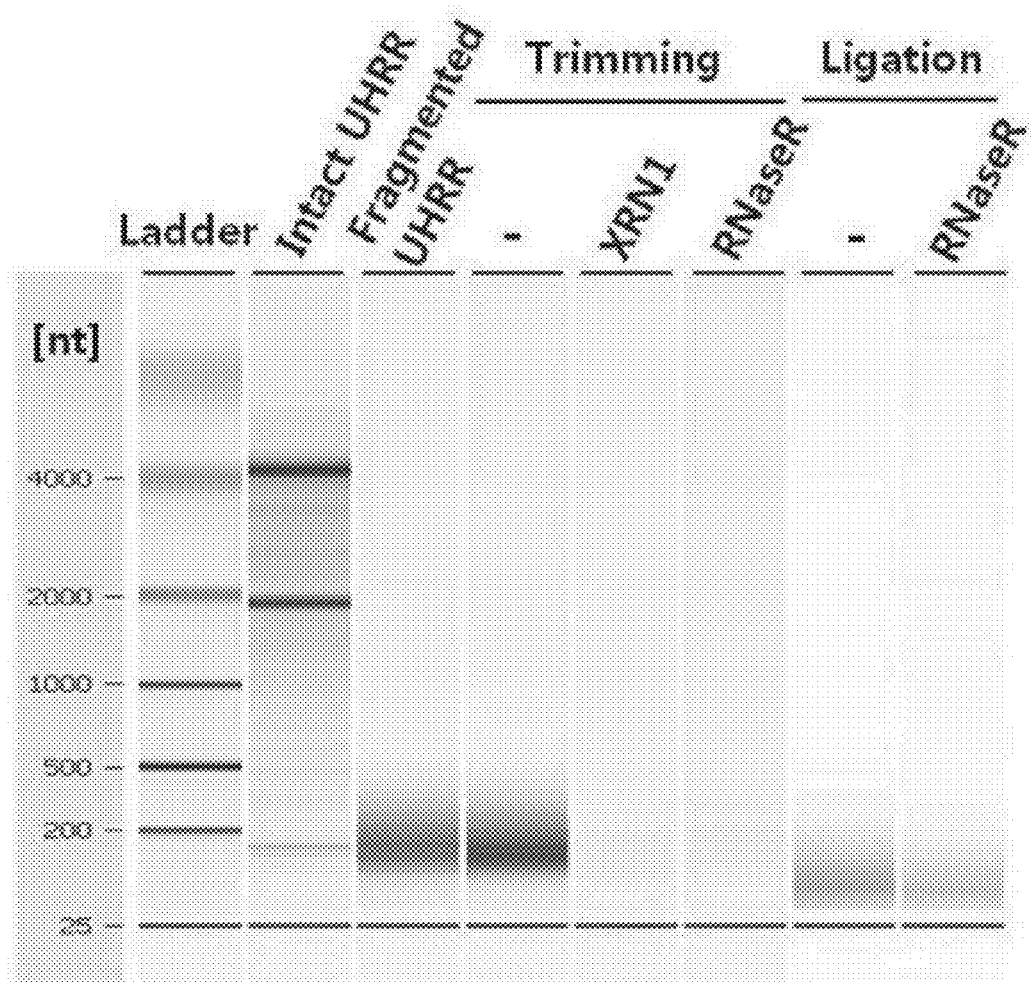
FIG. 9 shows electrophoresis result of products obtained by incubating products of trimming reaction and products of self ligation in the presence of XRN1 and RNaseR, respectively.

FIG. 9 shows electrophoresis result of products obtained by incubating products of trimming reaction and products of self ligation in the presence of XRN1 and RNaseR, respectively. In FIG. 9, Ladder is a size marker, Intact UHRR is UHRR without ultrasonic irradiation, Fragmented UHRR is UHRR with ultrasonic irradiation, Trimming is result of incubating the trimming products in the absence of XRN1 and RNaseR (−), in the presence of XRN1 or RNaseR, Ligation is result of incubating the self-ligation products in the absence of RNaseR (−), or in the presence of RNaseR.

(4) Multiple Displacement Amplification (MDA) Using Emulsion (4.1) Production and Polymerization of Water-in-Oil Droplets In 50 ml of mineral oils, 4.5% (v/v) of Span 80, 0.4% (v/v) of tween 80, and 0.05% (v/v) of Triton X-100 were mixed to obtain oil-surfactant mixture. 400 μl of the oil-surfactant mixture was placed in cryotube vial and mixed while stirring using 3×8 mm stir bar for about 5 minutes at 1000 rpm.

200 μl of the aqueous phase including 2 ng of the self-ligated UHRR (40 mM Tris-HCl pH 8.8, 6.4 mM (NH$_4$)$_2$SO$_4$, 53 mM KCl, 10.6 mM MgSO$_4$, 0.1% Triton X-100, 30 μM random hexamer, 1.33 mM dNTPs, 4.8 unit/μl Bst DNA polymerase, 16 unit/μl M-MLV reverse-transcriptase, 40 ng/μl T4 SSB, and 0.2% Antifoam) were added dropwise to the crytobe vial containing the oil-surfactant mixture and mixed while stirring for about 5 minutes at 1000 rpm.

As a result, emulsion including the aqueous phase were obtained. Droplets obtained from the emulsions had a diameter of 3.33 μm (CV 40%) in average. The droplets included components along with circular RNA, reverse transcription polymerase, and DNA polymerase required for polymerization, and amplification may be performed within the droplets. The circular RNA was eluted enough to include about 50% or less of the total droplets.

(4.2) Polymerization

The emulsion was incubated at 45° C. for about 15 hours to cause reverse transcription reaction and DNA-dependent DNA polymerase reaction. After the reaction, RNase was added and incubated to degrade the residual RNA.

After termination of the reaction, the emulsion was centrifuged at 13,000 g for about 5 minutes to remove oil phase. 1 ml of diethyl ether was added to the aqueous phase to destroy droplets of the emulsion and remove mineral oils.

(5) Determining of Correlation Before and after Amplification Using qPCR

Having the linear RNA of the fragmented UHRR and the self-ligation product as a template, a ratio of genes after amplification in the emulsion was measured to determine transcriptome amplification in the emulsion without a bias by using the circular RNA.

Then, 5 types of reference genes were selected, which are beta-Actin (ACTB), glyceraldehyde-3-phosphate dehydrogenase (GAPDH), beta-glucuronidase (GUSB), ribosomal protein, large P0 (RPLP0), and transferrin receptor p90, CD71 (TFRC). The circular RNA by self-ligation was introduced into the droplets of the emulsion and amplified according to (4.1) and (4.2).

A primer-probe set that was specific to the 5 types of reference genes was selected, and DNA was quantified by qRT-PCR having the linear RNA of the fragmented UHRR as a template (hereinafter, it is also called an amplicon from the linear RNA in the sample). Next, the linear RNA of the fragmented UHRR was circularized according to (1), (2), (3), (4.1), and (4.2), and 2 ng of the circular RNA as a template was introduced into the droplets of the emulsion and amplified by reverse transcription-rolling circle amplification (RT-RCA). As a result, 21 μg of the amplified product was obtained. Having this amplicon as a template and the primer-probe set that was specific to the 5 types of reference genes, DNA was quantified by using qRCR (hereinafter, it is also called as 'amplified product from the circular RNA'). In a comparison of the amplified product from the linear RNA in the sample with the amplified product from the circular RNA, correlation between the amount of the initial RNA and the amount of the DNA corresponding to the RNA that was amplified by the droplets of the emulsion in the circular RNA was determined. Table 2 shows the primer-probe set that was used in the experiment.

TABLE 2

| Target gene | Name | SEQ ID. No: |
|---|---|---|
| beta-Actin (ACTB) | B-actin_F | 11 |
| | B-actin_R | 12 |
| | B-actin_P | 13 |
| GAPDH | GAPDH_F | 14 |
| | GAPDH_R | 15 |
| | GAPDH_P | 16 |
| GUSB | GUSB_F | 17 |
| | GUSB_R | 18 |
| | GUSB_P | 19 |
| RPLPO | RPLPO_F | 20 |
| | RPLPO_R | 21 |
| | RPLPO_P | 22 |
| TFRC | TFRC_F | 23 |
| | TFRC_R | 24 |
| | TFRC_P | 25 |

Table 3 shows a Pearson correlation coefficient between the amplified product of the linear RNA in the sample and the amplified product of the circular RNA, that is, the amount of the initial RNA and the amount of the DNA corresponding to the RNA that was amplified by the droplets of the emulsion in the circular RNA.

TABLE 3

| Target gene | qRT-PCR product with a template of UHRR (RNA)* | qPCR product (DNA) with a template of emulsion amplification product (DNA) ** |
|---|---|---|
| Actin | $3.9 \times 10^6$ | $5.8 \times 10^8$ |
| GAPDH | $3.3 \times 10^6$ | $1.9 \times 10^8$ |
| RPLPO | $8.2 \times 10^5$ | $1.2 \times 10^8$ |
| TFRC | $6.1 \times 10^4$ | $1.5 \times 10^7$ |
| GUSB | $1.5 \times 10^4$ | $1.1 \times 10^7$ |
| Pearson correlation coefficient | | 0.87 |

As shown in Table 3, a Pearson correlation coefficient is 0.87, indicating that DNA was generated from target RNA to have a high similarity with a ratio of several species of RNA that were present in the beginning.

What is claimed is:

1. A method of determining a ratio of the amounts of two or more RNAs in a sample, the method comprising:
   a) providing a sample comprising two or more different RNAs;
   b) incubating the sample in the presence of: an enzyme that converts the 5'-cap structure into 5'-monophosphate to convert RNA having a 5'-cap structure in the sample into RNA having 5'-monophosphate;
   an enzyme that phosphorylates 5'-OH to convert RNA having 5-OH in the sample into RNA having 5'-monophosphate; and
   an enzyme that dephosphorylates a 3'-end to convert RNA having a 3'-phosphate group in the sample into RNA having 3'-OH,
   thereby producing a mixture comprising two or more different RNAs having a 5'-monophosphate and a 3'-OH in the sample;

c) subsequently incubating the mixture in the presence of an RNA ligase after step b), thereby producing circular RNAs from the two or more different RNAs having a 5'-monophosphate and a 3'-OH, wherein the RNA ligase catalyzes intramolecular ligation of each of the two or more different RNAs having a 5'-monophosphate and a 3'-OH;

d) incubating the circular RNAs in the presence of an RNA-dependent DNA polymerase, thereby producing DNAs from the circular RNAs;

e) from the DNAs, identifying sequences of DNA molecules that correspond to sequences of the two or more different RNAs in the sample and determining the amounts of the DNA molecules that correspond to the two or more different RNAs in the sample; and f) determining a ratio of the amounts of the DNA molecules that correspond to the two or more different RNAs in the sample, wherein the ratio of amounts of the DNA molecules correlates with the ratio of the amounts of the two or more different RNAs in the sample.

2. The method of claim 1, wherein the sample comprises at least one of:
RNA having a 5'-cap structure and 3'-OH;
RNA having a 5'-cap structure and 3'-monophosphate;
RNA having 5'-OH and 3'-monophosphate;
RNA having 5'-OH and 3'-OH;
RNA having 5'-monophosphate and 3'-OH; and
RNA having 5'-monophosphate and 3'-monophosphate.

3. The method of claim 1, wherein the sample comprises mRNA isolated from a biological sample.

4. The method of claim 1, wherein the sample comprises RNA degradation products.

5. The method of claim 1, wherein the sample comprises RNA isolated from a formalin-fixed paraffin-embedded (FFPE) tissue sample.

6. The method of claim 1, wherein the enzyme that converts the 5'-cap structure into 5'-monophosphate is tobacco acid pyrophosphatase (TAP), des-gamma-carboxy prothrombin (DCP), RNA 5' pyrophosphatase (RppH) or any combination thereof.

7. The method of claim 1, wherein the enzyme that converts RNA having 5'-OH into RNA having 5'-monophosphate is T4 polynucleotide kinase (PNK).

8. The method of claim 1, wherein the enzyme that converts RNA having a 3'-phosphate group into RNA having 3'-OH is T4 polynucleotide kinase (PNK).

9. The method of claim 1, wherein the RNA-dependent DNA polymerase has strand-displacing DNA polymerase activity.

10. The method of claim 1, wherein the RNA-dependent DNA polymerase comprises Bst DNA polymerase.

11. The method of claim 1, wherein step d) is performed in the presence of random primers.

12. The method of claim 1, further comprising annealing a poly(adenylate) sequence to the 3'-end of RNA in the sample by incubating the sample in the presence of poly(adenylate) polymerase before step c).

13. The method of claim 12, wherein step d) is performed in the presence of an oligo dT primer.

14. The method of claim 1, wherein the method further comprises, after step d), forming droplets comprising the circular RNAs and elements required for nucleic acid polymerization.

15. The method of claim 14, wherein the elements required for nucleic acid polymerization comprise reverse transcriptase, DNA-dependent DNA polymerase, or a combination thereof.

16. The method of claim 14, wherein step d) is performed under isothermal conditions.

17. The method of claim 14, wherein step d) is performed between about 40° C. and 50° C. without thermal cycling.

18. The method of claim 1, wherein step d) further comprises adding a DNA-dependent DNA polymerase simultaneously with the RNA dependent DNA polymerase, or incubating the DNAs produced from the circular RNAs in the presence of a DNA-dependent DNA polymerase after step d).

19. The method of claim 1, wherein step d) further comprises amplifying the DNAs produced from the circular RNAs.

* * * * *